United States Patent [19]

Harris

[11] 4,200,111
[45] Apr. 29, 1980

[54] SPECIMEN REMOVAL INSTRUMENT

[76] Inventor: Arthur M. Harris, 3349 W. Park Rd., Hollywood, Fla. 33021

[21] Appl. No.: 944,604

[22] Filed: Sep. 21, 1978

[51] Int. Cl.² .......................................... A61B 10/00
[52] U.S. Cl. ...................................................... 128/751
[58] Field of Search ............... 128/751, 752, 754, 755, 128/305, 321

[56] References Cited

U.S. PATENT DOCUMENTS

| | | | |
|---|---|---|---|
| 2,994,321 | 8/1961 | Tischler | 128/2 B |
| 3,001,522 | 9/1961 | Silverman | 128/2 B |
| 3,175,554 | 3/1965 | Stewart | 128/2 B |
| 3,404,677 | 10/1968 | Springer | 128/2 B |
| 3,895,636 | 7/1975 | Schmidt | 128/305 |
| 3,921,640 | 11/1975 | Freeborn | 128/321 X |
| 3,989,038 | 11/1976 | Neward | 128/2 B |

FOREIGN PATENT DOCUMENTS

| | | | |
|---|---|---|---|
| 245402 | 4/1912 | Fed. Rep. of Germany | 128/305 |
| 288576 | 5/1899 | France | 128/305 |

*Primary Examiner*—Kyle L. Howell
*Attorney, Agent, or Firm*—Oltman and Flynn

[57] ABSTRACT

A medical instrument for removing specimens from the lungs includes scissor-like cutting jaws and a tube which can be advanced toward the jaws to close them and slide over them. The jaws are biased to an open position when extended beyond the open end of the tube and include lateral projections which coact with longitudinal slots in the tube to guide the jaws relative to the tube.

8 Claims, 11 Drawing Figures

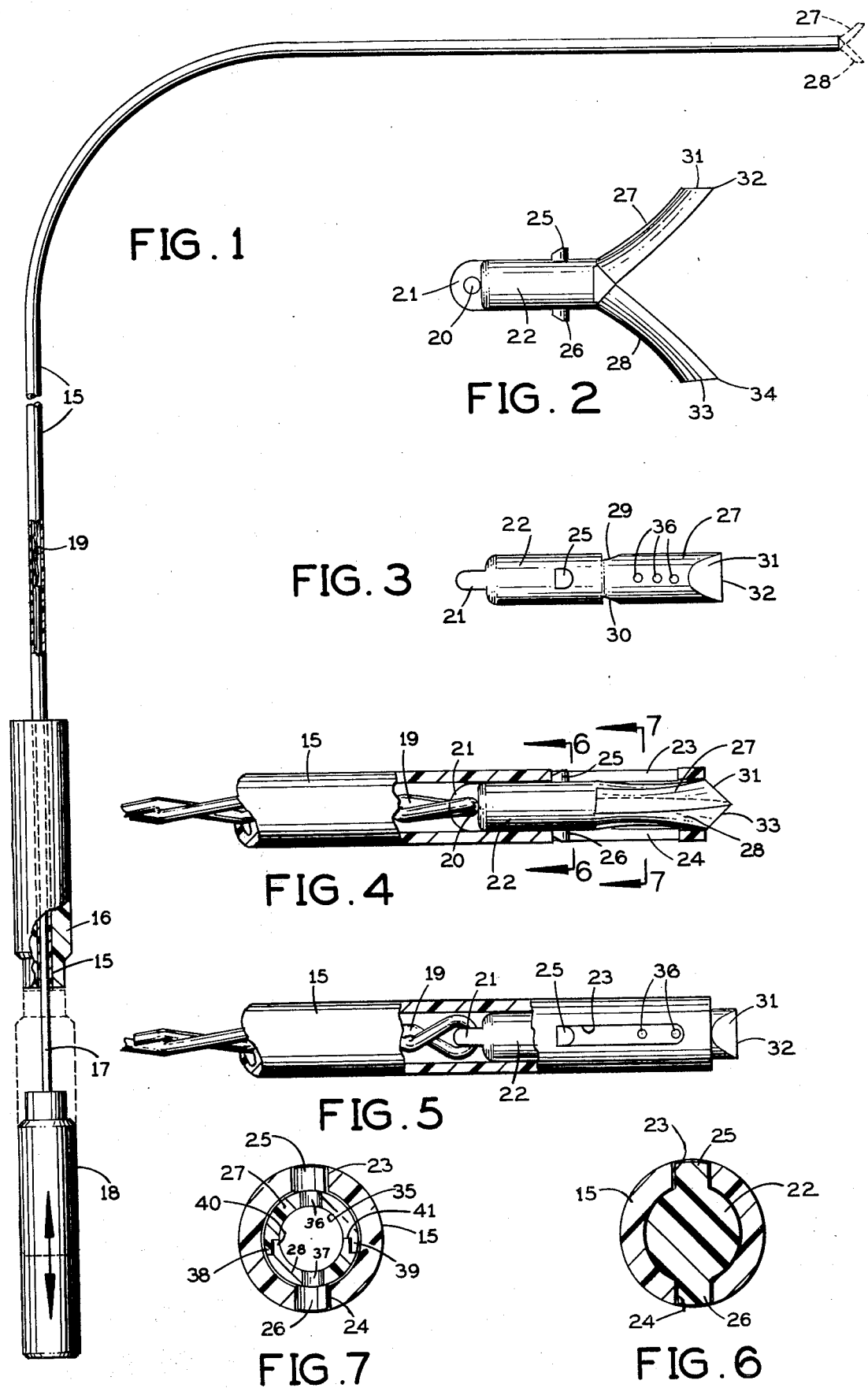

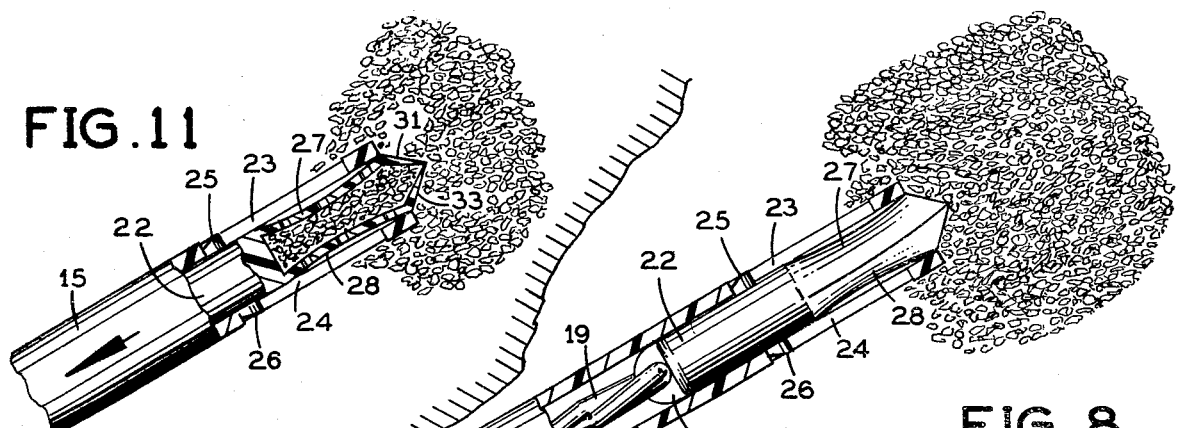
FIG. 11
FIG. 8
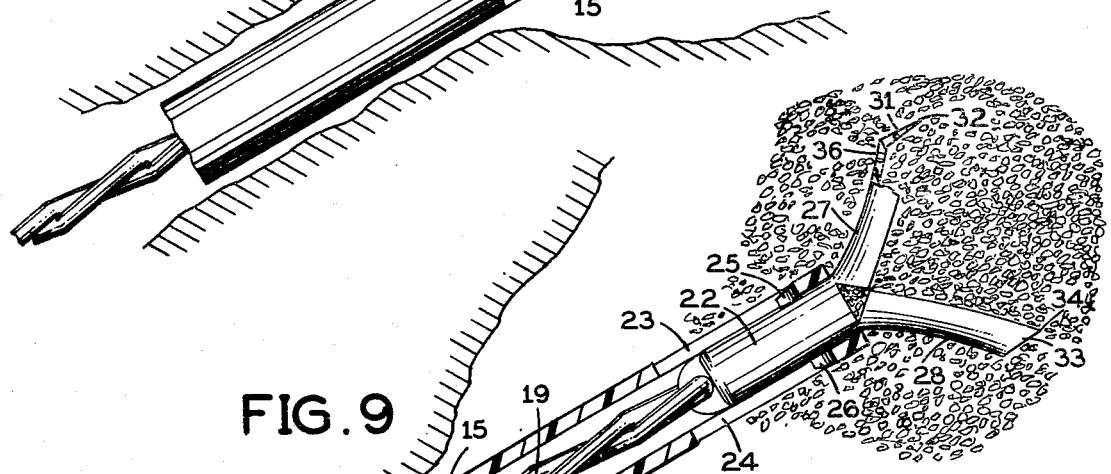
FIG. 9
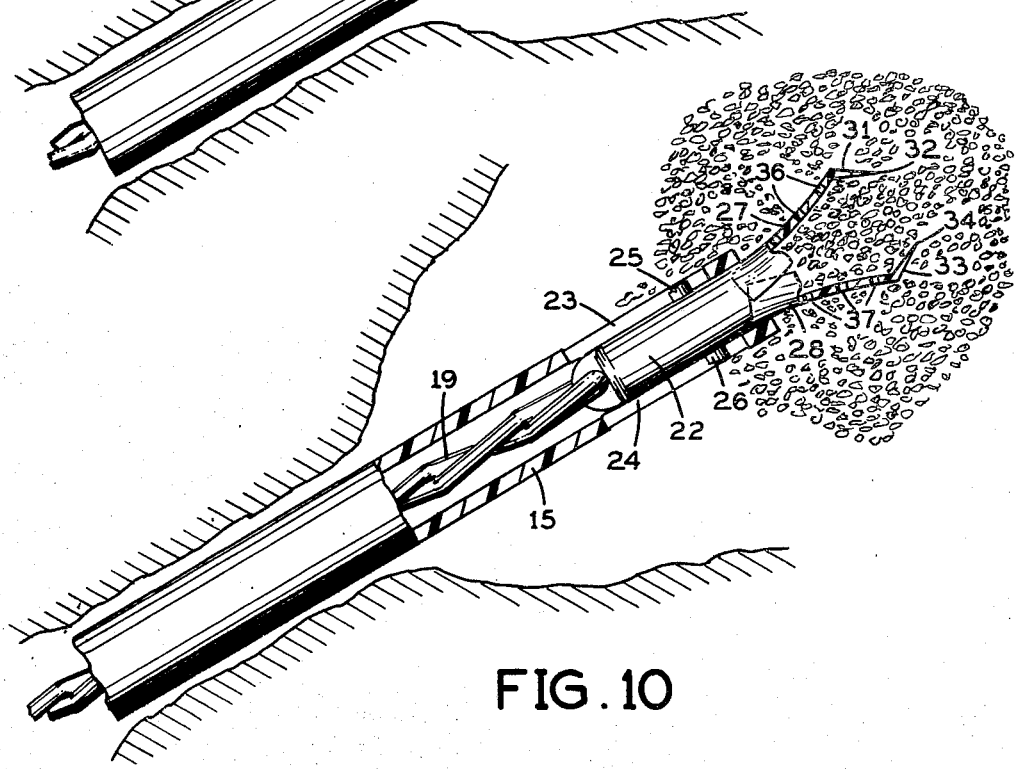
FIG. 10

SPECIMEN REMOVAL INSTRUMENT

BACKGROUND OF THE INVENTION

Instruments have been used heretofore for removing small specimens from a patient's lungs for analysis to assist in the diagnosis of the patient's condition. An elongated flexible tube has been inserted through the patient's throat and into the lung. A flexible push-pull element is operated from the inside of the tube. This push-pull element is operated from its upper end outside the patient. One or more brushes connected to the lower end of the push-pull element are movable by it between a retracted position inside the lower end of the tube and an extended position beyond the lower end of the tube for engaging and removing a specimen of the lung cell tissue and carrying it back into the tube when the push-pull element is retracted.

U.S. Pat. No. 2,739,585 shows such an arrangement having two wire brushes pivotally coupled to the lower end of the push-pull element. A spring biases these brushes apart when they are extended beyond the tube but permits them to move together when they are retracted into the tube.

Difficulties have been encountered with such insruments which use one or more brushes for removing the specimen because the brush itself is not always effective for this purpose. Also, the brush may be difficult to manufacture properly to serve its intended purpose.

SUMMARY OF THE INVENTION

The present invention is directed to a medical instrument for removing specimens from the lungs which uses cutting jaws for severing the specimen and carrying it into the elongated flexible tube when the tube is advanced. The jaws coact with each other to provide a scissors-like action in cutting the specimen from the lung.

Preferably, the jaws are connected to a head which is slidable in the lower end of the flexible tube. The jaws are formed with a built-in resilient bias which spreads them apart when they are pushed to an extended position beyond the lower end of the tube. The jaws are readily flexible so that they close on each other and sever the specimen when the tube is advanced.

A principal object of this invention is to provide a novel and improved instrument for removing a small specimen from a patient's lung.

Another object of this invention is to provide such an instrument having opposed jaws for severing a specimen and withdrawing it from the lung.

Further objects and advantages of this invention will be apparent from the following detailed description of a presently preferred embodiment thereof, which is shown in the accompanying drawings in which:

FIG. 1 is an elevational view of the present instrument with certain parts broken away for clarity and with the specimen-cutting jaws shown in phantom in their extended position;

FIG. 2 is an elevational view of the jaws and the slidable head to which they are attached;

FIG. 3 is a top plan view of the jaws and head as shown in FIG. 2;

FIG. 4 is a fragmentary view, partly in elevation and partly in section, showing the head and jaws retracted into the end of the tube in the FIG. 1 apparatus;

FIG. 5 is a top plan view of the FIG. 4 assembly;

FIG. 6 is a cross-section taken along the line 6—6 in FIG. 4;

FIG. 7 is a cross-section taken along the line 7—7 in FIG. 4;

FIG. 8 is a view similar to FIG. 4, showing the apparatus inserted into the lung to remove a specimen;

FIG. 9 is a view similar to FIG. 8, showing the jaws extended beyond the tube and expanded;

FIG. 10 is a view similar to FIG. 9 and showing the jaws being retracted into the tube and closing on each other; and FIG. 11 is a view similar to FIG. 10 and showing the jaws fully retracted and closed.

Before explaining the disclosed embodiment of the present invention in detail, it is to be understood that the invention is not limited in its application to the details of the particular arrangement shown since the invention is capable of other embodiments. Also, the terminology used herein is for the purpose of description and not of limitation.

Referring to FIG. 1, the present instrument comprises an elongated flexible tube 15 of suitable plastic which is rigidly secured at one end in a tubular collar 16. A metal rod 17 extends from a handle 18 slidably through the tube 15 inside the collar 16. Preferably, the rod 17 is about twice as long as the collar 16. The handle 18 is reciprocable toward and away from the collar 16 to slide the rod 17 along the flexible tube 15. The end of the rod 17 away from the handle 18 is connected to a two-strand, spirally-wound flexible metal wire 19, which extends slidably along the remainder of the flexible tube 15. The rod 17 and wire 19 together constitute a push-pull element which is slidably reciprocable in the tube 15 in response to displacement of the handle 18 toward and away from the collar 16. The flexible wire 19 is of a consistency which enables it to push and pull the head and jaws of the apparatus as will be described.

At the opposite end of the tube 15 from the collar 16 the wire 19 is looped through an opening 20 (FIG. 4) in an ear 21 on the end of a generally cylindrical head 22, which is slidable along the inside of tube 15. At this end the tube 15 is formed with diametrically opposed longitudinal slots 23 and 24 which slidably receive and guide corresponding lateral projections 25 and 26 on the head 22. With this arrangement the head 22 is prevented from turning and coming out of the tube 15 as it slides along the inside of the tube 15 at this end. The slots 23 and 24 terminate a short distance from this end of the tube 15. The other ends of the slots 23 and 24 stop the head when it is retracted.

A pair of opposed jaws 27 and 28 are formed integral with the end of the head 22 away from the push-pull wire 19. As shown in FIG. 3, the jaw 27 is notched at 29 and 30 immediately adjacent to its attachment to the head 22. The same is true of the other jaw 28. The exterior of each jaw is longitudinally arcuate in a concave sense.

The integral head-jaw body 22, 27 and 28 is molded of suitable plastic material so that when unstressed it assumes the position shown in FIG. 2, with the jaws spread apart. The jaws are sufficiently flexible, particularly where they are attached to the head 22, that they are brought together and close on each other when the tube is advanced, as shown in FIG. 4. The plastic material of the head 22 and jaws 27 and 28 is sufficiently resilient and has sufficient plastic "memory" that when the jaws are outside the tube 15 they immediately move apart to the unstressed condition shown in FIG. 2. Preferably, the head 22 and integrally attached jaws 27 and 28 are of polypropylene or other plastic material having similar properties.

As shown in FIG. 10, the jaw 27 has an end lip 31 which tapers to a sharp outer cutting edge 32. This end lip extends obliquely with respect to the remainder of jaw 27 in a direction away from the connection of this jaw to the head 22. The jaw 27 is of transversely arcuate, generally semi-circular cross-section, as shown in FIG. 7, so that it is concave viewed from below in this Figure.

The opposite jaw 28 has a similar end lip 33 which tapers to a sharp outer cutting edge 34. The end lip 33 extends obliquely with respect to the remainder of jaw 28 in a direction away from the connection of this jaw to the head 22. As shown in FIG. 7, the jaw 28 has an arcuate, generally semi-circular curvature opposite to that of the first jaw 27, so that when the jaws are closed they form a generally cylindrical recess 35 between their end lips 31, 33 and the head 22.

The outer cutting edge 32 on jaw 27 is straight and is disposed perpendicular to the axis of the head 22. This is also true of the outer cutting edge 34 on the opposite jaw 28. When the two jaws are drawn together, the cutting edges 32 and 34 register with and engage each other along their respective lengths.

The jaws are formed with openings 36 and 37 (FIG. 10) which register with the respective slots 23 and 24 in the tube 15 when the jaws are retracted into the tube. When the jaws are fully retracted, the end lips 31 and 33 form a point protruding slightly from the tube 15 so that the point can pierce tissue. One end of the slots 23 and 24 limits the head-jaws in the retracted position.

As shown in FIG. 7, the jaw 27 is cut away at the inside along its opposite longitudinal edges, so that along these edges at the outside this jaw presents projecting segments 38 and 39. The jaw 28 is of complementary shape along its opposite longitudinal edges, presenting projecting segments 40 and 41 which fit snugly but slidably inside the projecting segments 38 and 39 on jaw 27 when the jaws are together. Thus, the projecting segments 38, 40 along one side of the jaws and the projecting segments 34, 41 along the opposite side cooperate substantially in the same manner as the cutting edges of a scissors, when the jaws are brought together, to sever the specimen along each side of the jaws.

OPERATION

Before the present apparatus is inserted in the patient the knob 18 is retracted away from the collar 16, and acting through the push-pull element 17, 19 it positions the head 22 and jaws 27, 28 in the fully retracted position shown in FIG. 4. Now the end of the flexible tube 15 where the jaws 27, 28 are located is inserted through a bronchoscope into the patient's throat down into the lungs in a known manner.

When this end of the tube is at the desired location where a specimen is to be taken, as shown in FIG. 8, the handle 18 is pushed toward the collar 16, and it acts through the push-pull element 17, 19 to push the head 22 to the end of the tube 15 which is inside the patient's lungs. The jaws 27, 28 are pushed out of this end of the tube and due to their resiliency and exterior curvature they spread apart as shown in FIG. 9.

Now the tube 15 is advanced, and it compresses the jaws 27, 28 into the tube, as shown in FIG. 10. The jaws are sufficiently flexible that, acting against their inherent resilient bias, they move together as they slide into the tube 15. The jaws, as they are being received in the tube, first come together at the sliding, close overlap of the projecting segments 38, 40 and 39, 41 along their opposite sides. The scissors-like cutting action performed by these jaw segments begins first adjacent the sliding head 22 and then proceeds outward along the jaws as they are received more and more into the tube 15. Before the jaws reach the fully received position shown in FIG. 11 their outer cutting edges 32 and 34 come together and sever the specimen perpendicular to the lines along which it has already been cut progressively by the overlapping jaw segments 38, 40 and 39, 41.

With this arrangement, a small specimen is cut from the patient's lung and is confined between the closed jaws 27, 28 and the head 22. This cutting action provides a more reliable way of removing the specimen than the brush or brushes previously used for this purpose. The jaw openings 36, 37 and the aligned slots 23, 24 in the tube 15 permit excess liquid to escape from the severed specimen. The removed specimen is completely confined inside the tube so that it is fully protected as the tube is removed through the patient's throat and after such removal, as well. The instrument is disposable.

I claim:

1. In an instrument for obtaining a small specimen from the lungs comprising:
   an elongated flexible tube;
   a flexible push-pull element extending slidably through the tube;
   a head operatively connected to the inner end of said push-pull element and slidable in the inner end of the tube between a retracted position and an extended position;
   and opposed jaws operatively connected to said head at its inner end, said jaws being resiliently biased apart to project laterally beyond the tube at its inner end when said head is pushed to its extended position by said push-pull element, said jaws being movable laterally toward each other and slidable into the tube;
   the improvement wherein:
   said jaws have respective cutting edges which approach each other and sever a specimen from the lungs as said tube is advanced toward the jaws;
   and said jaws define a recess between them for holding the severed specimen;
   and further comprising
   means acting between said head and said tube for guiding the head lengthwise along the tube;
   said last mentioned means comprising longitudinal slots at diametrically opposed locations in the tube, and lateral projections carried by the head and slidably received respectively in said slots.

2. An apparatus according to claim 1, wherein said jaws are formed with openings behind said lips which register with said slots in the tube when the jaws are received in the tube.

3. An apparatus according to claim 1, wherein said jaws have a longitudinally arcuate exterior.

4. An apparatus according to claim 1, wherein said end lips slant to define a point, and said slots limit the retraction of said body and jaws so that said point projects from said tube for piercing purposes, and said slots limit the extension of said body and jaws so that at least a portion of said body remains in said tube.

5. In an instrument for obtaining a small specimen from the lungs comprising:
an elongated flexible tube;
a flexible push-pull element extending slidably through the tube;
a head operatively connected to the inner end of said push-pull element and slidable in the inner end of the tube between a retracted position and an extended position;
and opposed jaws operatively connected to said head at its inner end, said jaws being resiliently biased apart to project laterally beyond the tube at its inner end when said head is pushed to its extended position by said push-pull element, said jaws being movable laterally toward each other and slidable into the tube;
the improvement wherein:
said jaws have respective cutting edges which approach each other and sever a specimen from the lungs as said tube is advanced toward the jaws;
and said jaws define a recess between them for holding the severed specimen;
said jaws being integrally joined in cantilever fashion to the inner end of said head in a one-piece body of plastic material with a substantial plastic memory which spreads the jaws apart when outside said tube but permits the jaws to flex toward each other when received in the tube;
said jaws having respective end lips which terminate in cutting edges, with each of said end lips extending transverse to the remainder of the respective jaw and toward the end lip of the other jaw;
at least one of said jaws having projecting segments along its respective longitudinal edges which provide a cutting action as the jaws are drawn together by being received in the tube;
said jaws being of oppositely curved arcuate cross-section behind said lips to provide a rounded recess for holding the specimen; and
means acting between said head and said tube for guiding said head lengthwise along the tube;
said last mentioned means comprising longitudinal slots at diametrically opposed locations in the tube, and lateral projections carried by the head and slidably received respectively in said slots.

6. An instrument according to claim 5, wherein said jaws are formed with openings behind said lips which register with said slots in the tube when the jaws are received in the tube.

7. An instrument according to claim 5, wherein both of said jaws have projecting segments along their respective longitudinal edges which closely overlap slidably to provide a scissors-like cutting action as the jaws are drawn together.

8. An apparatus according to claim 5, wherein said jaws have a longitudinally arcuate exterior.

* * * * *